United States Patent [19] [11] 4,198,429
Bartmann et al. [45] Apr. 15, 1980

[54] ESTERS OF 5-METHYL-10,11-DIHYDROPROSTAGLANDIN-A₁

[75] Inventors: Wilhelm Bartmann, Bad Soden am Taunus; Gerhard Beck, Frankfurt am Main; Ulrich Lerch, Hofheim am Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 809,432

[22] Filed: Jun. 23, 1977

[30] Foreign Application Priority Data

Jun. 25, 1976 [DE] Fed. Rep. of Germany ....... 2628564

[51] Int. Cl.² ............... C07C 177/00; A61K 31/215
[52] U.S. Cl. ...................................... 424/305; 560/121
[58] Field of Search .................... 560/121; 424/305

[56] References Cited

U.S. PATENT DOCUMENTS

| 3,773,795 | 11/1973 | Bagli et al. | 260/345.7 |
| 3,873,607 | 3/1975 | Bernady et al. | 260/514 |
| 4,078,083 | 3/1978 | Babej et al. | 424/317 |
| 4,107,191 | 8/1978 | Smith | 260/408 |

Primary Examiner—Robert Gerstl
Attorney, Agent, or Firm—Curtis, Morris & Safford

[57] ABSTRACT

Prostaglandin esters of the formula

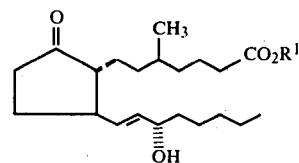

have valuable therapeutical properties.

2 Claims, No Drawings

ESTERS OF 5-METHYL-10,11-DIHYDROPROSTAGLANDIN-A$_1$

This invention relates to prostaglandin esters of formula I

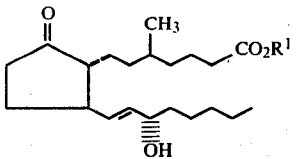

in which R$^1$ represents:
  a cycloalkyl radical having from 4 to 7 carbon atoms, or a linear or branched alkyl radical having from 3 to 10 carbon atoms, or
  a linear or branched alkyl radical having from 1 to 6 carbon atoms, which latter radical is substituted by
  (a) an optionally branched alkoxy radical having from 1 to 6 carbon atoms, or
  (b) a cycloalkyl radical having from 5 to 7 carbon atoms in which one CH$_2$ group can be replaced by an oxygen atom or
  (c) a cycloalkyloxy radical having from 5 to 7 carbon atoms, or
  (d) a phenyl radical, or
  (e) a phenoxy radical, or
  (f) a hydroxyl group.

The invention also provides a process for preparing an ester of formula I, which comprises
  (a) transforming 5-methyl-10,11-dihydroprostaglandin-A$_1$ of formula II

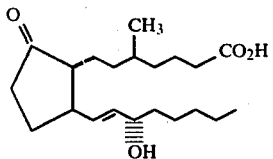

into a salt by reacting with a base and reacting the salt with an alkylating agent, or
  (b) esterifying the prostaglandin of formula II with a diazoalkane, or
  (c) esterifying the prostaglandin of formula II with an alkylaryl-triazene, or
  (d) reacting the prostaglandin of formula II with an alcohol in the presence of a water-binding agent, or
  (e) transesterifying an ester of the prostaglandin of formula II by reacting it with an alcohol R$^1$-OH in the presence of a base in an anhydrous medium, or
  (f) removing the CO$_2$R$^2$ group from a compound of formula III

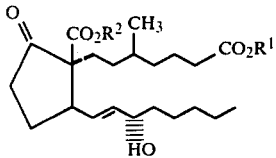

in which R$^1$ has the same meaning as in formula I and R$^2$ represents methyl or ethyl.

Preferred substituents R$^1$ are, for example:
n-propyl, n-butyl, n-pentyl, n-hexyl, n-heptyl, n-octyl, n-nonyl,
n-decyl, 2-propyl, 2-butyl, 2-pentyl, 2-hexyl, 2-heptyl, 2-octyl,
2-nonyl, 2-decyl, 3-pentyl, 3-hexyl, 3-heptyl, 3-octyl, 3-nonyl, 3-decyl, 4-octyl, 4-nonyl, 4-decyl, 5-nonyl, 5-decyl, 2-methylpropyl, 2-methylbutyl, 3-methylbutyl, 4-methylphenyl, 3,3-dimethylbutyl, 2-ethylbutyl, 3-methylhexyl, 5-methylhexyl, 4,4-dimethylpentyl, 6-methylheptyl, 4-ethylhexyl, 5,5-dimethylhexyl, 3-methyloctyl, 7-methyloctyl, 4,4-dimethylheptyl, 4-methylnonyl, 8-methylnonyl, 6-ethyloctyl, 7,7-dimethyloctyl, 5,5-dimethyloctyl, cyclobutyl, cyclopentyl, cyclohexyl, cycloheptyl, propoxymethyl, pentyloxymethyl, 2-(pent-3-yloxy)-ethyl, 2-(ethoxy)-ethyl, 2-(propoxy)-ethyl, 2-(butoxy)-ethyl, 2-(pentyloxy)-ethyl, 2-(hexyloxy)-ethyl,
2-(hex-2-yloxy)-ethyl, 2-(hex-3-yloxy)-ethyl, 3-(methoxy)-propyl,
3-(ethoxy)-propyl, 3-(propoxy)-propyl, 3-(butoxy)-propyl, 3-(pentyloxy)-propyl, 3-(hexyloxy-)propyl, 3-(2-methylpropoxy)-propyl,
3-(2-ethylbutoxy)-propyl, 3-(3-methylbutoxy)-propyl, 3-(3,3-dimethylbutoxy)-propyl, 3-(2-butoxy)-propyl, 4-(methoxy)-butyl,
4-(ethoxy)-butyl, 4-(propoxy)-butyl, 4-(butoxy)-butyl, 4-(pentyloxy)-butyl, 4-(hexyloxy)-butyl, 4-(4-methylpentyloxy)-butyl,
4-(pent-3-yloxy)-butyl, 3-(3-methylpentyloxy)-2-methylpropyl,
5-(methoxy)-pentyl, 5-(ethoxy)-pentyl, 5-(propoxy)-pentyl,
5-(butoxy)-pentyl, 5-(pentyloxy)-pentyl, 5-(hexyloxy)-pentyl,
5-(1-methylpentyloxy)-pentyl, 5-(2-ethylbutoxy)-pentyl, 3-(pentyloxy)-2-ethylpropyl, 6-(methoxy)-hexyl, 6-(ethoxy)-hexyl, 6-(propoxy)-hexyl, 6-(butoxy)-hexyl, 6-(prop-2-oxy)-hexyl, 4-(methoxy)-3-ethylbutyl, 5-(ethoxy)-2-methylpentyl, cyclopentyloxymethyl,
cyclohexyloxymethyl, cycloheptyloxymethyl, 2-(cyclopentyloxy)-ethyl, 2-(cyclohexyloxy)-ethyl, 2-(cycloheptyloxy)-ethyl,
3-(cyclopentyloxy)-propyl, 3-(cyclohexyloxy)-propyl, 2-(cyclohexyloxy)-propyl, 4-(cyclopentyloxy)-butyl, 4-(cyclohexyloxy)-butyl,
3-(cyclopentyloxy)-2-methylpropyl, 5-(cyclopentyloxy)-pentyl,
5-(cyclohexyloxy)-pentyl, 6-(cyclopentyloxy)-hexyl, cyclopentylmethyl, cyclohexylmethyl, cycloheptylmethyl, 2-(cyclopentyl)-ethyl, 2-(cyclohexyl)-ethyl, 2-(cycloheptyl)-ethyl, 3-(cyclopentyl)-propyl, 3-(cyclohexyl)-propyl, 1-(cyclopentyl)-prop-2-yl, 4-(cyclohexyl)-butyl, 4-(cyclohexyl)-but-2-yl, 5-(cyclopentyl)-pentyl,
1-(cyclopentyl)-pent-3-yl, 2-(cyclohexyl)-pentyl, 6-(cyclopentyl)-hexyl, 6-(cyclohexyl)-hexyl, 3-tetrahydrofurylmethyl, 3-tetrahydrofurfuryl, 2-tetrahydropyranylmethyl, 3-tetrahydropyranylmethyl,
4-tetrahydropyranylmethyl, 2-(tetrahydrofuryl-2)-ethyl, 3-(tetrahydrofuryl-2)-propyl, 2-(tetrahydropyran-2-yl)-ethyl, 2-(tetrahydropyran-4-yl)-ethyl, 3-(tetrahydropyran-2-yl)-propyl, 4-(tetrahydrofuryl-2)-butyl, 4-(tetrahydropyran-4-yl)-butyl, 5-(tetrahydrofuryl-2)-pentyl, 5-(tetrahydropyran-2-yl)-pentyl, 6-(tetrahydrofuryl-3)-hexyl, 6-(tetrahydropyran-4-yl)-hexyl, benzyl, 2-phenylethyl, 3-phenylpropyl, 2-phenylpropyl, 4-phenylbutyl, 4-methyl-4-phenylpentyl, 5-phenylpentyl, phenoxymethyl, 2-phenoxyethyl, 3-phenoxypropyl, 2-phenoxypropyl, 3-phenoxybutyl, 5-phenoxypentyl, 4-phenoxy-3-methylbutyl, 6-phenoxyhexyl, 2-hydroxyethyl, 3-hydroxypropyl, 4-hydroxybutyl, 3-hydroxybutyl, 5-hydroxypentyl, 4-hydroxypentyl, 6-hydroxyhexyl, 5-hydroxyhexyl, 4-hydroxyhexyl, 3-hydroxyhexyl.

The 5-methyl-10,11-dihydroprostaglandin of formula II used as starting material in processes (a) to (d) can be prepared by a process as described in DT-OS 2,346,706 while the starting compound of formula III for process (f) can be obtained by a process as described in DT-OS 2,331,081.

According to process (a) esters of formula I can be prepared by transforming the prostaglandin of formula II into a salt using a base and reacting the salt with a suitable alkylating agent.

Suitable bases are alkali metal alcoholates, for example sodium methylate, sodium ethylate or potassium tert.butylate; metal hydrides, for example sodium hydride or lithium hydride; metal carbonates, for example sodium carbonate or sodium bicarbonate; metal hydroxides, for example sodium hydroxide or potassium hydroxide; metal amides, for example sodium amide; organo-metal compounds, for example lithium triphenylmethyl or lithium butyl; amines, for example triethyl amine, 1,5-diazabicyclo[3,4,0]-nonene-5, pyridine, or quinoline.

As alkylating agents there can be used compounds of the formula $R^1$-X in which X represents an electronegative atom or an electro-negative group and $R^1$ has the same meaning as in formula I. X preferably stands for bromine or iodine or an alkyl or aryl-sulfonic acid radical.

Suitable solvents for the alkylating reaction are ethers, fo example tetrahydrofurane, dioxane or 1,2-dimethoxyethane; alcohols such as methanol, ethanol or tert.butanol, preferably dipolar aprotic solvents such as acetonitrile, sulfolane, N-methylpyrrolidone, dimethyl formamide, dimethyl acetamide, or dimethyl sulfoxide.

According to a preferred embodiment of the process of the invention 1 to 1.5 times the molar amount of sodium methylate is added to a solution of compound II in dimethyl formamide and the alkylating agent, for example alkyl iodide, is added after approximately 10 minutes. The reaction mixture is stirred under argon at 50° C. and its treatment is continued as soon as the carboxylic acid of formula II is fully consumed, generally after 1 to 3 hours. The reaction mixture is distributed between toluene and water, the organic phase is concentrated by evaporation under reduced pressure and the residue is optionally subjected to chromatography on silica gel.

The diazo compounds required for the preparation of the esters of formula I according to process (b) are described in Houben-Weyl, Methoden der Organischen Chemie, volume X/4, pages 473 et seq. They can also be synthesized by analogous methods.

The reaction of compounds II with diazo compounds is suitably carried out in a hydrocarbon as solvent, for example cyclohexane, chlorinated hydrocarbons such as methylene chloride or chloroform, and preferably an ether such as diethyl ether, tetrahydrofuran or dioxane.

A preferred mode of esterification with the diazo compounds consists in adding 1.1 to 1.5 times the molar amount of the diazo compound in an ether, while cooling with ice, to a solution of the compound of formula II. When the reaction is finished the solvent is evaporated and, if desired, the residue is purified by chromatography.

According to process (c) an ester of formula I is prepared by reacting an alkyl-aryl-triazene with the compound of formula II. Esterifications of this type are described, for example, in Tetrahedron Letters 21, 758 (1961) or in Org. Synth. 48, 102 (1968).

A preferred mode of execution of this process consists in adding a solution of compound II in a non-polar solvent, for example diethyl ether or cyclohexane, to the triazene, for example 1-alkyl-3-p-tolyl-triazene. The mixture is allowed to stand for 3 to 24 hours at room temperature, washed with aqueous sodium dihydrogen phosphate solution and then sodium bicarbonate solution, whereupon the ester is isolated by concentration of the organic phase. If desired, the crude product is purified by chromatography on $SiO_2$.

Esters of formula I can also be prepared according to process (d) by reacting the prostaglandin of formula II with an alcohol in the presence of a suitable water-binding agent, for example a carbodiimide such as dicyclohexyl carbodiimide, or sterically hindered dimethyl-formamido-dialkyl acetals, for example dimethyl-formamido-dineopentyl acetal.

According to a preferred embodiment of this process the solution of compound II in methylene chloride or chloroform is stirred at 0° to 25° C. with dicyclohexyl carbodiimide and, after 30 to 60 minutes, the alcohol is added, optionally together with a base such as pyridine or picoline. After having stirred for another 2 to 5 hours at room temperature, the reaction mixture is diluted with a non polar solvent, for example cyclohexane, the insoluble matter is separated by filtration and the concentrated filtrate is subjected to chromatography on silica gel.

One ester of formula I can be transformed into another one by transesterification. It proved advantageous, for example, to prepare esters deriving from secondary alcohols by reacting the compound of formula II with diazomethane to give the methyl ester ($R^1$=$CH_3$), which is then transesterified with an alkali metal alcoholate in the corresponding alcohol. After neutralization with glacial acetic acid and removal of excess alcohol the reaction product can be purified by chromatography.

Esters of formula I can be prepared according to process (f) by eliminating the ester group in 8-position from compounds of formula III in an anhydrous dipolar aprotic solvent, for example dimethyl formamide, hexamethyl phosphoric acid triamide (HMPT) or dimethyl sulfoxide, in the presence of a salt, for example sodium or potassium cyanide, lithium chloride or lithium bromide, at a temperature of from 40° to 180° C.

According to a preferred embodiment of this process, a diester of formula III as described in DT-OS 2,331,081 is heated for 1 to 4 hours at 70° to 80° C. with sodium cyanide in anhydrous HMPT. After cooling, the reaction mixture is neutralized with glacial acetic acid, ice water is added and the reaction product is extracted with benzene or ether. If desired, it can be purified by chromatography.

The compounds of formula I according to the invention have valuable therapeutical properties. For example, partially they have a contracting effect on the uterus and partially they have hypotensive and sodium diuretic properties, but more especially they have a spasmolytic effect on the bronchial muscles which can be utilized for treating an acute attack of asthma. As compared with 5-methyl-10,11-dihydroprostaglandin-A$_1$ (II), the esters of formula I have a stronger and/or longer lasting effect, which is especially interesting for therapeutical application.

To test the bronchospasmolytic activity of the compounds of the invention the following experiments were carried through:

TEST ACCORDING TO KONZETT-RÖSSLER

To test the bronchospasmolytic activity the respiratory volume was measured by the method of Konzett-Rössler, according to which the air volume is measured which is taken up by the lung when the maximum inflation pressure is maintained constant and a constant volume is offered by high pressure respiration. Capacity variations in the respiratory tract result in an increase or decrease of the amount of air taken up by the lung under the given constant inflation pressure.

As test animals male white Guinea pigs having a weight of from 400 to 500 grams were used which had been anesthesized with 10 mg/kg i.p. of Evipan and 200 mg/kg i.p. of urethane. The substance to be tested was administered by means of a catheter in the V. jugularis. The positive pressure respiration depended on the normal respiratory volume of the test animal and could be adapted suitably and readily to the individual test animal. In the tests carried through the pressure indicated by Rosenthal and Dervinis of 80 mm H$_2$O was used. During the recovery phase after a bronchospastic reaction the flexible hose leading to the water manometer was clamped off for a short period of time in order to open deflating lung segments. The respiration frequency amounted to 64–72 per minute. The respiratory volume was measured according to the slightly modified Konzett-Rössler method wherein the piston recorder was replaced by a back-pressure tube according to Fleisch (type 0000). The occuring pressure difference was recorded by a difference pressure recorder of the type Statham PM 97 CT. To record the measured values a multi-channel recorder of Messrs. Hellige was used. The substance to be tested was used in the form of a standard solution in absolute alcohol. Directly prior to the start of the test it was diluted to the required final concentration with phosphate buffer (pH 7.4). The asthmogenic solution was prepared with double distilled water.

As asthmogenic agents histamine dihydrochloride, acetyl choline chloride and sertonine creatinine sulfate were used. To reduce the error resulting from individual differences in the bronchospasm intensity with a uniform dose of asthmogenic agent, the dosage unit was chosen such that an about 70 to 80% decrease of the absorption capacity of the lung was obtained. The experimental data were subjected to the regression analysis according to the probit transformation and the equation of the straight lines of regression y=a+b log x was calculated. In this manner the average inhibition dose (ID$_{50}$=the dose which inhibits the effect of the asthmogenic agent to 50% of the initial value) was found. Additionally, the results obtained by carrying out a simple variance analysis in the Duncan Test were compared with the control.

To produce bronchospasmolytic aerosols an ultrasound atomizer of the type Monaghan M 650 was used. The concentration of the liquid to be atomized depended on the dose to be atomized within 1 minute and the density of the aerosol, which was 0.02 ml/min. According to the indications of the producer the particles had a size in the range of from 1 to 8 microns, predominantly 3 microns.

Results:

In the modified Konzett-Rossler test as described above the ID$_{50}$ of 5-methyl-10,11-dihydroprostaglandin-A$_1$ (formula II) was found to be 9 ng/animal for the spasm initiated by serotonin, 10 ng/animal for the spasm caused by acetylcholine and 5 ng/animal for the bronchospasm caused by histamine. The duration of action did not exceed 10 minutes. As compared therewith the esters of the present invention had a stronger and/or longer lasting bronchospasmolytic effect.

| Example | ID$_{50}$ values (ng/animal) | | | duration of effect minutes |
|---------|-----------|---------------|-----------|---------|
| | histamine | acetylcholine | serotonin | |
| comp. II | 5    | 10   | 9    | 10    |
| 3       | 0.63 | 6.9  | 1.2  | 15–20 |
| 7       | 0.4  | 0.88 | 0.86 | 10–20 |
| 2       | 4.2  |      |      | 30–45 |
| 1       | 1    | 3    |      | 30    |
| 6       | 7.5  |      |      | 60    |
| 4       | 7    |      |      | 20–25 |
| 9       | 1    |      |      | 25    |

The compounds of the invention can be used either alone or in admixture with pharmacologically acceptable carrier materials, the use as aerosol being preferred. To this end, the active compounds are brought into a suitable form of administration, for example they are dissolved with the usual, physiologically tolerable solvents not having an irritative taste, such as water or ethanol, or they are mixed with low molecular weight alkyl esters of higher fatty acids, for example myristic acid isopropyl ester, optionally with addition of tensioactive substances as dissolving intermediary or stabilizers, for example sorbitan or pentaerythritol fatty acid esters and filled into aerosol bombs with dosing valve together with a usual inert propellant. As individual dose about 0.01 to 10 μg/kg and as daily dose 0.1 to 50 μg/kg are suitable.

The novel compounds can be used in combination with other active substances, above all expectorants, for example Bisolvon, β-sympathomimetic agents, for example Salbutamol or Aludrin, or antitussive agents, for example codein.

The following examples illustrate the invention.

EXAMPLE 1

5-Methyl-10,11-dihydroproxtaglandin-A$_1$ n-hexyl ester (a) 33 mg (0.6 mmol) of sodium methylate are added, while stirring under argon, to a solution of 141 mg (0.4 mmol) of 5-methyl-10,11-dihydroprostaglandin-A$_1$ (of formula II) in 2 ml of absolute DMF. After 5 minutes, 127 mg (0.6 mmol) of 1-iodohexane are added and the reaction mixture is heated to 50° C. After 3 hours, the reaction mixture is distributed between toluene and water, the organic phase is dried and concentrated by evaporation. The residue is chromatographed on 6 g of SiO$_2$, eluant: 50 ml of CCl$_4$, then 100 ml of CCl$_4$/acetone 97:3 and 100 ml of CCl$_4$/acetone 95:5.

R$_f$=0.49 (CCl$_4$/acetone 7:3)

NMR: δ 5.5–5.8 (m, 2H) CH=CH 3.9–4.3 (m, 1H) CH—OH super-imposed by —OCH$_2$— (t, 2H)

(b) 176 mg (0.5 mmol) of 5-methyl-10,11-dihydroPGA$_1$ are dissolved in 10 ml of chloroform, 180 mg of dicyclohexyl carbodiimide are added while cooling with ice and the mixture is stirred for one hour. Next, 1 ml of 1-hexanol and 0.4 ml of pyridine are added and the mixture is stirred for 4 hours at room temperature. The solvent is removed under reduced pressure, the residue is taken up in carbon tetrachloride, undissolved matter, if any, is eliminated by suction filtration and the product is purified by chromatography as described above. The compound obtained is identical with the ester obtained as described sub (a).

EXAMPLE 2

5-Methyl-10,11-dihydroprostaglandin-A$_1$ n-decyl ester

The reaction is performed as described in Example 1(a) with 5-methyl-10,11-dihydroprostaglandin-A$_1$ and i-iododecane.

$R_f$=0.24 (CCl$_4$/acetone 9:1)
NMR: δ 5.54–5.75 (m, 2H) CH=CH 4.1 (m, 1H and t, 2H) C$\underline{H}$—OH and O—CH$_2$

EXAMPLE 3

5-Methyl-10,11-dihydroprostaglandin-A$_1$ n-butyl ester (a) The reaction is performed as described in Example 1(a) using 5-methyl-10,11-dihydroprostaglandin-A$_1$ and 1-iodobutane.

$R_f$=0.43 (CCl$_4$/Acetone 7:3)
NMR: δ 3.95–4.3 (3H) C$\underline{H}$—OH, O—CH$_2$.

(b) In the atmosphere of an inert gas a solution of 282 mg (0.8 mmol) of 5-methyl-10,11-dihydroprostaglandin-A$_1$ (formula II) in 3 ml of ether is added to a solution of 210 mg (1.1 mmol) of 1-butyl-3-p-tolyltriazene in 2 ml of ether. The mixture is allowed to stand overnight at room temperature, the solvent is removed under reduced pressure and the residue is purified by chromatography on silica gel.

As regards its properties the product obtained is identical with that of Example 3(a).

EXAMPLE 4

5-Methyl-10,11-dihydroprostaglandin-A$_1$ 4,4-dimethylphenyl ester

The reaction is performed as described in Example 1(a) with 5-methyl-10,11-dihydroprostaglandin-A$_1$ and 4,4-dimethyl-1-iodopentane.

$R_f$=0.53 (CCl$_4$/acetone 7:3)
NMR: δ=4.07 (t, 2H and m, 1H) C$\underline{H}$—OH and OCH$_2$ 5.55–5.75 (m, 2H) CH=CH 0.9 (15H) CH$_3$.

EXAMPLE 5

5-Methyl-10,11-dihydroprostaglanin-A$_1$ cyclohexylmethyl ester

The reaction is performed as described in Example 1(a) with 5-methyl-10,11-dihydroprostaglandin-A$_1$ and cyclohexyl-iodomethane.

$R_f$=0.55 (CCl$_4$/acetone 7:3)
NMR: δ 5.5–5.7 (m, 2H) CH=CH 4.1 (m, 1H) C$\underline{H}$—OH, 3.9 (d, 2H) O—CH$_2$

EXAMPLE 6:

5-Methyl-10,11-dihydroprostaglandin-A$_1$ cyclohexyl ester (a) 70.2 mg (0.2 mmol) of 5-methyl-10,11-dihydroprostaglandin-A$_1$ in 2 ml of absolute ether are reacted with 0.4 ml of a 0.6 molar solution of diazomethane in ether. After stirring for 30 minutes at room temperature, the solvent is evaporated under reduced pressure and a solution of 50 mg of sodium in 1 ml of anhydrous cyclohexanol is added to the crude methyl ester. The mixture is heated to 30°–35° C. while stirring and after 2 hours neutralized with glacial acetic acid. The reaction mixture is distributed between water and toluene, the organic phase is dried with magnesium sulfate and the solvent is evaporated, at the end in a high vacuum. The oily residue is chromatographed on 5 g of SiO$_2$ using as eluant 50 ml of carbon tetrachloride and 50 ml each of carbon tetrachloride/acetone 97.3 and 95:5.

$R_f$=0.55 (CCl$_4$/acetone 7:3)
NMR: δ 5.5–5.7 (m, 2H) CH=CH 4.75 (m, 1H) CO$_2$—CH 4.1 (m, 1H) C$\underline{H}$—OH.

(b) In an atmosphere of argon 506 mg (1 mmol) of 8-ethoxycarbonyl-5-methyl-10,11-dihydroprostaglandin-A$_1$ cyclohexyl ester and 100 mg (2 mmols) of NaCN in 10 ml of anhydrous hexamethylphosphoric acid triamide are heated for 3 hours at 80° C. While cooling with icewater the reaction mixture is then adjusted to pH 6 with glacial acetic acid and the reaction mixture distributed between benzene and water. The organic phase is washed with water, dried with anhydrous magnesium sulfate and concentrated by evaporation. The residue can be purified by chromatography on silica gel.

The product obtained is identical with the product described in Example 6(a).

EXAMPLE 7

5-Methyl-10,11-dihydroprostaglandin-A$_1$-2-ethoxyethyl ester 4 ml of a 1 molar solution of 2-ethoxydiazoethane (Ann. 679, 42) are added, while stirring at room temperature, to 103.3 mg (0.3 mmol) of 5-methyl-10,11-dihydroprostaglandin-A$_1$ in 4 ml of absolute ether. After 15 minutes, the solvent is removed under reduced pressure and the residue chromatographed on 6 g of SiO$_2$. Eluant: 50 ml of carbon tetrachloride, thereafter carbon tetrachloride/acetone 95:5.

$R_f$=0.44 (CCl$_4$/acetone 7:3).
NMR: δ 5.4–5.6 (m, 2H) CH=CH, 3.9–4.25 (m, 3H) CO$_2$—CH$_2$ and C$\underline{H}$—OH, 3.4–3.7 (m, 4H) CH$_2$—O—CH$_2$.

EXAMPLE 8

5-Methyl-10,11-dihydroprostaglandin-A$_1$-4-ethoxybutyl ester

The reaction is carried out as described in Example 1(a) using 5-methyl-10,11-dihydroprostaglandin-A$_1$ and 4-ethoxy-1-iodo-butane.

$R_f$=0.13 (CCl$_4$/acetone 9:1).
NMR: δ 5.5–5.7 (m, 2H) CH=CH, 3.9–4.25 (m, 3H) CO$_2$CH$_2$ and C$\underline{H}$—OH, 3.25–3.7 (m,4H) CH$_2$—O—CH$_2$.

EXAMPLE 9

5-Methyl-10,11-dihydroprostaglandin-A$_1$-3-phenylpropyl ester

The reaction is carried out as described in Example 1(a) with 5-methyl-10,11-dihydroprostaglandin-A$_1$ and 3-phenyl-1-iodopropane.

$R_f$=0.55 (CCl$_4$/acetone 7:3).
NMR: δ 7.26 (s, 5H) arom. protons, 5.5–5.7 (m, 2H) CH=CH, 4.0–4.3 (m, 3H) CO$_2$—CH$_2$ and C$\underline{H}$—OH.

EXAMPLE 10

5-Methyl-10,11-dihydroprostaglandin-$A_1$-4-phenoxybutyl ester

The reaction is carried out as described in Example 1(a) using 5-methyl-10,11-dihydroprostaglandin-$A_1$ and 4-phenoxy-1-iodobutane.

$R_f=0.18$ ($CCl_4$/acetone 9:1).

NMR: δ 6.7–7.4 (m, 5H) arom. protons, 5.5–5.7 (m, 2H) CH=CH, 3.8–4,3 (m, 5H) O—$CH_2$ and C$\underline{H}$—OH.

EXAMPLE 11

5-Methyl-10,11-dihydroprostaglandin-$A_1$-6-hydroxyhexyl ester

The reaction is carried out as described in Example 1(a) using 5-methyl-10,11-dihydroprostaglandin-$A_1$ and 6-hydroxy-1-iodo-hexane.

$R_f=0.27$ ($CCl_4$/acetone 7:3).

NMR: δ 5.5–5.7 (m, 2H) CH=CH, 4.1 (m, 1H and t, 2H) C$\underline{H}$—OH and $CO_2$—$CH_2$, 3.65 (t, 2H) $\underline{CH_2}$—OH.

EXAMPLE 12

5-Methyl-10,11-dihydroprostaglandin-$A_1$ pentyl ester

The reaction is carried out as described in Example 1(a) using 5-methyl-10,11-dihydroprostaglandin-$A_1$ and 1-iodopentane.

$R_f=0.14$ $CCl_4$/acetone 9:1).

NMR: δ 5.5–5.65 (m, 2H) CH=CH, 4.1 (m, 1H) C$\underline{H}$OH, superimposed by 4.05 (t, 2H) $CH_2O$.

EXAMPLE 13

5-Methyl-10,11-dihydroprostaglandin-$A_1$ 2-cyclohexyloxyethyl ester

The reaction is carried out as described in Example 7 with 5-methyl-10,11-dihydroprostaglandin-$A_1$ and 2-cyclohexyloxydiazoethane (prepared according to Ann. 679, 42).

$R_f=0.17$ ($CCl_4$/acetone 9:1).

NMR: δ 5.5–5.7 (m, 2H) CH=CH, 3.8–4.3 (m, 4H) $CO_2$—$CH_2$, C$\underline{H}$—OH,

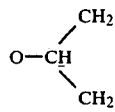

3.5 (t, 2H) $\underline{CH_2}$-O-cyclohexyl

EXAMPLE 14

5-Methyl-10,11-dihydroprostaglandin-$A_1$ 2-butoxyethyl ester

The reaction is carried out as described in Example 7 with 5-methyl-10,11-dihydroprostaglandin-$A_1$ and 2-butoxydiazoethane.

$R_f=0.16$ ($CCl_4$/acetone 9:1).

NMR: δ 5.5–5.7 (m, 2H) CH=CH, 3.85–4.3 (m, 3H) C$\underline{H}$—OH and $CO_2CH_2$, 3.5–3.7 (m, 4H) $CH_2$—O—$CH_2$.

EXAMPLE 15

5-Methyl-10,11-dihydroprostaglandin-$A_1$ hept-4-yl ester

The reaction is carried out as described in Example 6 with 5-methyl-10,11-dihydroprostaglandin-$A_1$ methyl ester and sodium 4-heptanolate $R_f=0.21$ ($CCl_4$/acetone 9:1).

NMR: δ 5.5–5.7 (m, 2H) CH=CH, 4.65 (m, 1H) $CO_2$—CH, 4.1 (m, 1H) C$\underline{H}$—OH.

What is claimed is:

1. A compound of the formula

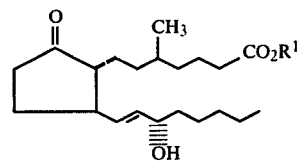

wherein $R^1$ is
cycloalkyl having from 4 to 7 carbon atoms, or
linear or branched alkyl having from 3 to 10 carbon atoms, or
linear or branched alkyl having from 1 to 6 carbon atoms which is substituted by
(a) linear or branched alkoxy having from 1 to 6 carbon atoms, or by
(b) cycloalkyl having from 5 to 7 carbon atoms, wherein one $CH_2$ group can be replaced by an oxygen atom, or by
(c) cycloalkyloxy having from 5 to 7 carbon atoms, or by
(d) phenyl, or by
(e) phenoxy, or by
(f) hydroxy.

2. A pharmaceutical composition for the treatment of bronchial spasms which comprises a bronchospasmolytically-effective amount of a compound as in claim 1 together with a pharmaceutical carrier therefor.